Figure 1:
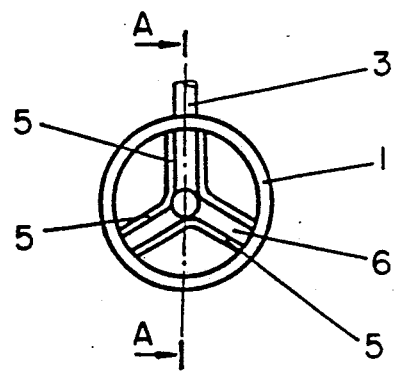

United States Patent
Meriläinen et al.

[11] Patent Number: 5,088,332
[45] Date of Patent: Feb. 18, 1992

[54] GAS FLOW RESTRICTING AND DIRECTING DEVICE INTENDED FOR FLOW MEASUREMENT

[75] Inventors: Pekka T. Meriläinen; Kari Eskelinen; Hannu E. Hänninen, all of Helsinki, Finland

[73] Assignee: Instrumentarium Corporation, Finland

[21] Appl. No.: 447,210

[22] Filed: Dec. 7, 1989

[30] Foreign Application Priority Data

Dec. 16, 1988 [FI] Finland .................................. 885756

[51] Int. Cl.$^5$ .......................... G01F 1/46; A61B 5/087
[52] U.S. Cl. .................................... 73/861.65; 128/725
[58] Field of Search ........... 73/861.52, 861.65, 861.66, 73/861.67; 128/725

[56] References Cited

U.S. PATENT DOCUMENTS

| | | | |
|---|---|---|---|
| 1,145,220 | 7/1915 | Wilkson | 73/861.66 |
| 2,706,409 | 4/1955 | Preston | 73/861.66 |
| 3,449,954 | 6/1969 | Brown | 73/861.65 |
| 3,590,473 | 7/1971 | Carlson | 73/861.67 |
| 3,910,113 | 10/1975 | Brown | 73/861.65 |
| 4,036,054 | 7/1977 | Goulet | 73/861.66 |
| 4,047,521 | 9/1977 | Kramer et al. | 73/861.65 |
| 4,170,134 | 10/1979 | Nathan | 73/861.65 |
| 4,372,170 | 2/1983 | Dehart et al. | |
| 4,403,514 | 9/1983 | Osborn | |
| 4,481,829 | 11/1984 | Shortridge | 73/861.66 |
| 4,546,655 | 10/1985 | Victor | 73/861.66 |

FOREIGN PATENT DOCUMENTS 699939 11/1953 United Kingdom .
2052074 1/1981 United Kingdom .

Primary Examiner—Herbert Goldstein
Attorney, Agent, or Firm—Andrus, Sceales, Starke & Sawall

[57] ABSTRACT

A gas flow directing and restricting device intended for flow measurement and having bilaterally located apertures (2) communicating via a measuring tube (3) to a measuring device (4) for measurement of pressure difference. Starting from aperture (2) and leading towards the inside boundary of flow tube (1), there are one or more baffles (5) either perpendicular to the longitudinal axis of tube (1) or inclined forwards against the direction of flow, whereby said baffles guide the flowing gas to aperture (2).

22 Claims, 1 Drawing Sheet

GAS FLOW RESTRICTING AND DIRECTING DEVICE INTENDED FOR FLOW MEASUREMENT

The invention relates to a gas flow restricting and directing device intended for flow measurement and having bilaterally located apertures communicating with a measuring device for measurement of pressure difference.

In hospitals both in intensive care and during operations it is necessary to perform human respiration artificially using a mechanical respirator. The unhindered flow of the gases to and from the lungs is naturally of vital importance. The functioning of the gas passages can be monitored both by measuring the contents of the expired gases and by measuring the flows and pressure. Monitoring of the carbon dioxide content of the expired gas is in extensive routine use in operating theaters. Flow and pressure measurements are, however, essential additional quantities both from the point of view of safety and to enable the calculation of quantities describing the mechanical functioning and gas exchange of the lungs.

There are several types of flow sensor suitable in principle. The most commonly employed are turbine, hot wire, ultrasonic and pressure-loss sensors. Numerous problems, however, are associated with measurements under clinical conditions. Flow is measured at the end of a so-called intubation tube inserted into the patient's trachea. The sensor is then exposed to both moisture and mucus secretions coming from the trachea. It is obvious that fouling very easily affects the operation of turbine and hot-wire sensors in particular. Ultrasonic sensors are more tolerant of fouling, but are dependent on changes in the flow profile and in the temperature and composition of the gas, requiring sophisticated compensation.

Flow in a tube can, as is well known, be laminar or turbulent. In the laminar case the pressure difference across a flow restricting body placed in the path of flow is directly proportional to the rate of flow. For turbulent flow the pressure difference is a function of the square of the rate of flow. The well-known and commonly used Fleisch type of flow sensor is based on a laminar flow resistance which is constructed by partitioning the space inside a tube into a multiplicity of small tubes in each of which the flow remains laminar over the range of measurement concerned. A consequence of this, however, is that the sensor easily becomes blocked.

The simplest turbulent flow resistance is a plate disposed perpendicular to the tube and having a hole in the center or the inverse body of said plate, in which a circular disk is suspended in the center of the flow path. A baffle plate of this type is reasonably tolerant of fouling but nevertheless the larger the signal, i.e. pressure difference, that is desired for a given rate of flow the smaller the hole that must be used whereon the effect of fouling becomes relatively more evident. The greatest problem, however, is the dependence on the flow profile. Because an intubation tube is curved, the flow profile of the gas is not symmetrical with respect to the central axis of the tube since centrifugal force presses the gas molecules towards the wall on the outside of the curve. The signal then becomes dependent on the curvature of the tube and on the angle of rotation of the sensor with respect to the tube. The construction of the sensor itself is generally made asymmetrical with respect to the longitudinal axis by the input apertures of the pressure difference measuring tubes.

An object of the present invention is to eliminate the said problems. An object of the invention is to provide a device for directing and restricting gas flow, and in particular the flow of respiratory gases, which is independent of the flow profile of the gas. An object of the invention is further to provide a device for directing and restricting gas flow which functions reliably even in dirty conditions.

The characteristic features of the device according to the invention are given in the accompanying claims.

The present invention relates to a gas flow directing and restricting device intended for flow measurement by means of which device the signal arriving at the measuring device is maximized and the effects of an asymmetrical flow profile are automatically eliminated.

The basis of the invention is that the gas flow directing and restricting device located in the path of the gas flow and across which the pressure difference is measured, comprises vanes disposed laterally with respect to the direction of flow which direct part of the gas flow into an aperture leading to a measuring device. Said measuring device is advantageously a pressure difference measuring device which compares the pressures prevailing on either side of said flow directing and restricting device.

The vanes which lie in the path of flow are advantageously disposed radially about the aperture leading to the measuring device. Said vanes should in the preferred case be at least three in number and should preferably be disposed symmetrically about the aperture. The width of said vanes or the area of the surface confronting the flow and the number of said vanes are mutually interdependent factors. A suitable angle between said vanes is 360° divided by the number of vanes. The vanes can either be perpendicular or inclined at e.g. 20° with respect to the plane perpendicular to the longitudinal axis of the tube.

The surface of the vanes facing upstream should preferably have channels leading towards the aperture to enhance the ability of the vanes to conduct part of the flow, e.g. that following along the boundary of the tube, into the aperture leading to the measuring device. An especially suitable location for the aperture is at the center of the tube.

When the gas flow, as for example in human respiration, is of alternating direction it is advantageous to locate similar flow restricting and directing devices to face in each of the upstream directions of gas flow, which devices thus direct gas flow from either direction along the vanes disposed laterally across the path of gas flow to the measuring device.

An advantage of vanes disposed laterally across the path of gas flow is that they do not collect very much of the liquid and mucus coming along the patient's respiratory passages compared with the prior known devices described above. Liquid and mucus secretions which travel mainly along the boundary of the tube can be further hindered from reaching the aperture leading to the measuring device e.g. by directing the flow occurring in the immediate vicinity of the boundary of the tube away from the paths leading to the aperture or possibly by allowing the flow occurring in the immediate vicinity of the boundary of the tube to continue in its forward path unhindered. For this reason the present flow directing and restricting device does not become blocked either.

Figure 2:
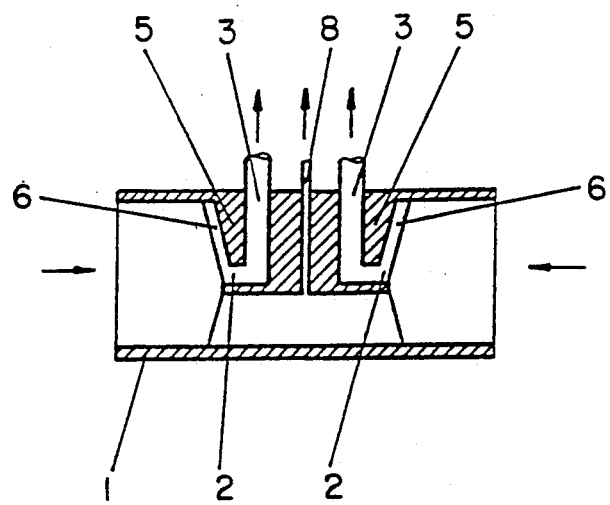
Figure 3:
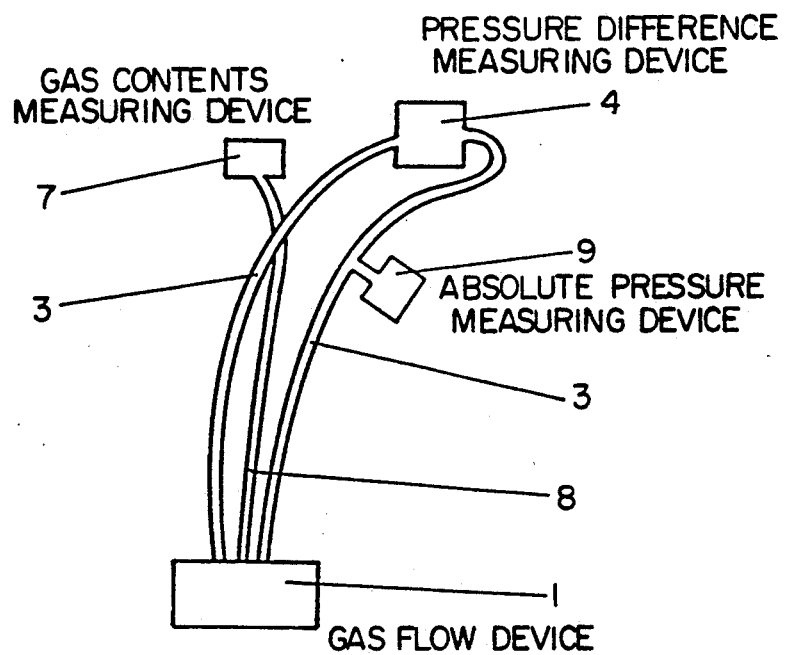

The invention is described in greater detail by reference to the accompanying drawings, in which FIG. 1 shows the gas flow restricting and directing device intended for flow measurement in accordance with the invention in a direct front view of the upstream side, FIG. 2 shows a section along A-A through the flow restricting and directing device of FIG. 1, FIG. 3 shows a general view in which the gas flow restricting and directing device intended for flow measurement in accordance with the invention is in a tube and is connected to a measuring device.

The construction of the gas flow restricting and directing device intended for flow measurement in accordance with the invention is shown in FIGS. 1 and 2. In these figures is illustrated in particular a device according to the invention which is suitable for the measurement of flow occurring alternately from two opposing directions such as, for example, the measurement of respiration. The device in question operates on the principle of the ram effect. On either side of the device in tube 1 there are apertures 2. Tubes 3, which are perpendicular with respect to the flow, lead from said apertures to a measuring device 4, which is advantageously a device measuring pressure difference. Around the apertures 2 at the ends of tubes 3 are vanes or baffles 5, which in this case are three in number. The angle between them is 120°. This arrangement collects ram pressure uniformly from every direction and shifting of the flow profile does not affect the result.

On the surfaces of vanes 5 facing upstream there are advantageously channels 6 directing the flow coming towards said vanes to aperture 2. The bottom of said channel should preferably be perpendicular to the direction of flow. In the inclined case the radial component of the pressure tends to carry secretions which may have collected at the bottom of the channel towards aperture 2 and further into tube 3.

Since for measurement of the gas contents a small continuous sample flow is sucked out of the flow to a gas contents measuring device 7, for which purpose a separate adapter has to be attached to the end of the intubation tube, it is especially advantageous if flow measurement can be obtained in the space required for this gas flow directing and restricting device. This situation is achieved in the present invention and the gas sample is sucked from a tube 8 which is located between tubes 3 leading to measuring device 4.

By connecting to one of the pressure measurement tubes additionally an absolute pressure measuring device 9 in accordance with FIG. 3 the bronchial pressure also be measured, which provides additional information regarding the situation e.g. in the event of disconnection or blockage of a tube. Further, from this together with flow data it is possible to calculate lung mechanical quantities.

The invention is in no way restricted to the embodiments presented above, and the various details of the invention can be varied within the scope of the patent claims.

In connection with the description presented above a certain measuring device 2 has been described as a pressure-difference measuring device. It is self-evident that also separate pressure measuring devices, or even some other measuring device, can be connected to each of tubes 3.

We claim:

1. A gas flow pickup device for use in measuring the properties of a flowing gas containing liquid or viscid material, said device comprising:

a tube through which the gas flows, said tube having an axis and an inner wall spaced from said axis and along which wall the material tends to settle as the gas flows through the tube;

aperture means within said tube providing first and second apertures opening into said tube, said apertures being spaced apart along the axial direction of the tube and communicating with conduit means providing an output from said device, said apertures being located generally on said axis of said tube so that fouling of said apertures by the material is lessened; and at least one baffle means mounted within said tube and coupled to said aperture means, said baffle means comprising the sole means for positioning said aperture means in said tube, said baffle means having at least one surface facing the gas flow in the tube and extending inwardly from said tube to said aperture means adjacent one of said apertures for collecting and guiding the pressure generated by the gas flowing in the tube toward the apertures.

2. A device according to claim 1 wherein said aperture means provides a firs aperture opening in one axial direction in said tube and a second aperture opening in the opposite axial direction in said tube.

3. A device according to claim 2 wherein said apertures lie generally normal to the axis of said tube.

4. A device according to claim 1 wherein said baffle means has surfaces facing the gas flow in both directions in said tube.

5. A device according to claim 1, wherein said baffle means includes three baffles coupled to said aperture means at locations circumferentially spaced about the aperture means.

6. A device according to claim 1, wherein said baffle means includes four baffles coupled to said aperture means at locations circumferentially spaced about said aperture means.

7. A device according to claim 1, wherein said at least one surface facing the gas flow is perpendicular to the axis of the tube.

8. A device according to claim 1, wherein said at least one surface is inclined from a perpendicular to the axis of the tube in a manner such that said surface slants toward said aperture as it extends from said tube to said aperture means.

9. A device according to claim 1 wherein said baffle means has surfaces lying parallel to the axis of the tube and along which gas flowing in the tube passes.

10. A device according to claim 9 wherein said apertures are axially spaced in the tube and wherein said parallel surfaces span the axial spacing between said apertures.

11. A device according to claim 9 wherein said baffle means has a generally parallelopipedal configuration.

12. A device according to claim 1, wherein said device includes means for taking a gas sample from the tube.

13. A device according to claim 1, further defined as a gas flow pickup device for measuring flow properties of respiratory gases flowing in the tube.

14. A device according to claim 1, further defined as including pressure difference measuring apparatus coupled to said conduit means.

15. A device according to claim 14, further defined as including an absolute pressure measuring means coupled to said conduit means.

16. A device according to claim 14, wherein said conduit means includes a conduit communicating with each of said apertures, and wherein said pressure measuring apparatus includes separate pressure measuring devices connected to said conduits.

17. A gas flow pickup device for use with a measuring apparatus measuring the flow properties of a gas containing liquid or viscid material, said device comprising:

a tube through which the gas flows, said tube having an axis and an inner wall spaced from said axis and along which wall the material tends to settle as the gas flows through the tube;

aperture means in the tube said aperture means providing a first aperture that opens in the tube in one axial direction along the tube and a second aperture that opens in the tube in the opposite axial direction along the tube, said first aperture being spaced from said second aperture along the axial direction in the tube, said apertures lying generally normal to the axial direction and communicating with conduit means couplable to the measuring apparatus, said apertures being located generally on said axis of said tube so that fouling of said apertures by the material is lessened; and at least one baffle means mounted with said tube and coupled to said aperture means for positioning said aperture means in said tube, said baffle means extending inwardly from the tube to said aperture means and having surfaces lying generally parallel to the axial direction in the tube so that gas flowing in the said tube may pass along said surfaces, said baffle means having means for collecting and guiding the pressure generated by the gas flowing in the tube to the apertures.

18. A device according to claim 17 wherein said baffle means surfaces are further defined as spanning the axial spacing between said apertures.

19. A gas flow pickup device for use in measuring the properties of a flowing gas, said device comprising:

a tube through which the gas flows, said tube having an axis;

aperture means within said tube providing first and second apertures opening into said tube, si apertures being spaced from the inner wall of the tube and being spaced apart along the axial direction of the tube, said apertures communicating with conduit means providing an output from said device; and at least one baffle means mounted within said tube and coupled to said aperture means, said baffle means comprising the sole means for positioning said aperture means in said tube, said baffle means having at least one surface facing the gas flow in the tube and extending inwardly from said tube to said aperture means adjacent one of said apertures, said surface of said baffle means facing the gas flow having a concavity that extends along the surface from said tube to said aperture means for collecting and guiding the pressure generated by the gas flowing in the tube toward the apertures.

20. A device according to claim 19, wherein said surface has a channel that extends along the surface from said tube to said aperture means.

21. A gas flow pickup device for use in a measuring the properties of a flowing gas, said device comprising:

a tube through which the gas flows, said tube having an axis;

aperture means within said tube providing first and second apertures opening into said tube, said apertures being spaced from the inner wall of the tube and being spaced apart along the axial direction of the tube, said apertures communicating with conduit means providing an output from said device; and at least three baffle means mounted within said tube and coupled to said aperture means at locations circumferentially spaced about the aperture means, said baffle means comprising the sole means for positioning said aperture means in said tube, said baffle means having surfaces facing the gas flow in the tube and extending inwardly from said tube to said aperture means adjacent one of said apertures for collecting and guiding the pressure generated by the gas flowing in the tube toward the apertures.

22. A device according to claim 21 including four baffles coupled to said aperture means at locations circumferentially spaced about said aperture means.

* * * * *

UNITED STATES PATENT AND TRADEMARK OFFICE
CERTIFICATE OF CORRECTION

PATENT NO. : 5,088,332

DATED : February 18, 1992

INVENTOR(S) : Pekka Merilainen et al

It is certified that error appears in the above-identified patent and that said Letters Patent is hereby corrected as shown below:

CLAIM 1, Col. 4, line 24, after "the" third occurence insert --said one of said --.   CLAIM 2, Col. 4, Line 26 delete "firs" and substitute therefor ---first---;  CLAIM 17, Col. 5, Line 30 delete "with" and substitute therefor ---within---;  CLAIM 19, Col. 6, Line 2 delete "si" and substitute therefor ---said---;  CLAIM 19, Col. 6, Line 19, after "the" second occurrence insert ---said one of said---;  CLAIM 21, Col. 6, Line 23, after "in" delete ---a---;  CLAIM 21, Col. 6, line 43, after "the" third occurence insert --said one of said --.

Signed and Sealed this

Twentieth Day of April, 1993

Attest:

MICHAEL K. KIRK

*Attesting Officer*       Acting Commissioner of Patents and Trademarks